United States Patent [19]

Huber et al.

[11] 4,208,338
[45] Jun. 17, 1980

[54] CYANO DIHYDRO FURANONES

[75] Inventors: Ulrich Huber, Zurich; Hans J. Wild, Meilen, both of Switzerland

[73] Assignee: Givaudan Corporation, Clifton, N.J.

[21] Appl. No.: 32,446

[22] Filed: Apr. 23, 1979

Related U.S. Application Data

[62] Division of Ser. No. 928,136, Jul. 26, 1978.

[30] Foreign Application Priority Data

Aug. 11, 1977 [LU] Luxembourg ........................ 77955
Dec. 14, 1977 [LU] Luxembourg ........................ 78691

[51] Int. Cl.² .................................................. C07D 307/32
[52] U.S. Cl. ............................................... 260/347.8
[58] Field of Search ...................................... 260/347.8

[56] References Cited
PUBLICATIONS

Leonard et al., Chemical Abstracts, vol. 51 (1957) 17,873h.
Vartanyan et al., Chemical Abstracts, vol. 63 (1965) 14,794b.

*Primary Examiner*—Richard Raymond
*Attorney, Agent, or Firm*—Thomas Cifelli, Jr.; Robert F. Tavares

[57] ABSTRACT

This deals with a process for making furanones having the formula:

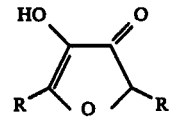

I wherein R represents a hydrogen atom or the methyl or ethyl group.

These furanones are known flavoring substances.

The furanones I are made by cleaving cyanohydrin from the following novel compounds:

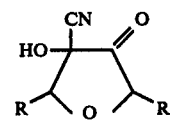

II

The novel compounds II are made by oxidizing the novel compounds:

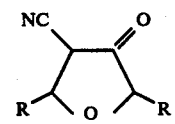

III

8 Claims, No Drawings

CYANO DIHYDRO FURANONES

This is a division, of application Ser. No. 928,136 filed July 26, 1978.

FIELD OF THE INVENTION

This invention relates to novel cyano compounds and to furanones.

SUMMARY OF THE INVENTION

See the Abstract of The Invention, supra.

DESCRIPTION OF THE PREFERRED EMBODIMENTS

The furanones manufactured in accordance with the present invention are compounds of the general formula:

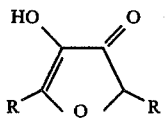   I wherein R represents a hydrogen atom or the methyl or ethyl group.

It will be appreciated that in the formulae herein the R-symbols can have the same significance or a different significance.

The process provided by the present invention for the manufacture of the compounds of formula I comprises subjecting a compound of the general formula:

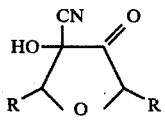   II wherein R has the significance given earlier,
to the cyanohydrin cleavage.

The cyanohydrin cleavage can be carried out thermally or can be base-catalysed.

In the thermal cyanohydrin cleavage, a compound of formula II is conveniently heated to a temperature of ca 50° C. to 400° C., especially to ca 80°–250° C. Addition of an acid, e.g. $H_2SO_4$ is advantageous.

In the base-catalysed cyanohydrin cleavage, a compound of formula II is treated with a base, the base being conveniently used in catalytic amounts (e.g. with 1/1000–1/10 equivalents) or, however, also in larger (e.g. molar) amounts.

The nature of the base is not critical. Examples of bases which can be used are inorganic bases such as alkali metal hydroxides (e.g. sodium hydroxide), alkaline earth metal hydroxides (e.g. calcium hydroxide and magnesium hydroxide), alkali metal carbonates (e.g. sodium carbonate and potassium carbonate), alkali metal bicarbonates (e.g. sodium bicarbonate), ammonia, other basic salts (e.g. sodium phosphate, potassium hydrogen phosphate and borax), basic buffer systems (e.g. sodium bicarbonate/sodium carbonate, potassium hydrogen phosphate/potassium phosphate etc), organic bases (e.g. amines such as triethylamine, pyridine, morpholine etc), salts of organic acids with strong bases (e.g. sodium acetate, formate, oxalate, citrate and lactate) or basic ion exchangers (e.g. Amberlite IRA 400, Dowex 2, etc).

The base-catalysed cyanohydrin cleavage can be carried out in the gas phase or in the liquid phase. The presence of a solvent is not necessary, but is convenient.

The base-catalysed cyanohydrin cleavage is preferably carried out at a temperature of 50°–200° C., especially ca 100° C.

The nature of the solvent is not critical. A polar solvent such as water, ammonia or an alcohol, or an apolar solvent such as toluene, benzene, ether, petroleum ether etc can be used.

Preferred systems are basic ion exchangers in the $OH^\ominus$ form/water, or salts of organic acids such as sodium oxalate/water or pyridine/toluene at a temperature of ca 100° C.

The compounds of formula II are novel and also form part of the present invention.

The compounds of formula II can advantageously be prepared by oxidising a compound of the general formula

   (III)

wherein R has the significance given earlier.

Especially suitable oxidising agents are alkali metal caroates (e.g. $KHSO_5$). The preferred oxidising agent is "Caroat" (Trade Mark) ($KHSO_5$ containing [small amounts of ] $KHSO_4$ and $K_2SO_4$).

The caroate is conveniently used in an amount of 1–2.5 equivalents, especially 1.1–1.5 equivalents.

The oxidation is preferably carried out in a polar solvent such as water, an alcohol, acetone or acetonitrile or in a mixture of such solvents.

The pH of the medium in which the oxidation is carried out conveniently amounts to ca 3–11, such as can be generated by appropriate buffer systems of the carbonate, phosphate, citrate, borate, $NH_3/NH_4^+$ or oxalate type in a manner known per se.

The oxidation can be carried out at a temperature of, for example, between $-10°$ C. and 60° C., preferably between 0° C. and 20° C.

The compounds of formula III are novel and also form part of the present invention.

The compounds of formula III can advantageously be obtained by reacting a nitrile of the general formula

   (IV)

with an ester of the general formula

   (V)

wherein R has the significance given earlier and $R_1$ represents a lower alkyl group.

The reaction of a nitrile of formula IV with an ester of formula V is conveniently carried out at an elevated temperature; for example, at 40°–100° C. and especially at about 60° C. The reaction can also be carried out at a lower temperature (e.g. at room temperature). However, at this temperature the formation of byproducts is observed. These byproducts must be removed (e.g. by extraction in a weak basic medium) during the working-up of the compound of formula III.

The molar ratio of nitrile of formula IV to ester of formula V preferably amounts to 1:1.

The reaction is conveniently carried out in the presence of a base and in a solvent.

As the base there are conveniently used 1-2 equivalents, especially 1-1.3 equivalents, of a strong base; for example, a hydride such as sodium hydride, an amide such as potassium amide, lithium diisopropylamide etc, a hydroxide such as sodium hydroxide, an alcoholate such as sodium ethylate or potassium isopropylate or a metal such as sodium or potassium.

As the solvent there is especially used a polar, preferably aprotic, solvent.

Examples of such solvents are ethers such as tetrahydrofuran, dioxan, diglyme, diethyl ether and diisopropyl ether, nitro compounds such as nitromethane and nitrobenzene, nitriles such as acetonitrile, dimethylformamide, dimethyl sulphoxide etc. Ethers are especially preferred.

Examples of protic solvents are alcohols such as tert-.butanol and isopropanol.

The compounds of formula I are known. They are useful as flavouring substances.

The following Examples illustrate the present invention:

EXAMPLE 1

(a) 130 g (1.1 mol) of ethyl lactate are added dropwise to 24 g (1 mol) of sodium hydride in 500 ml of tetrahydrofuran. 73.7 g (1.1 mol) of crotonic acid nitrile in 60 ml of tetrahydrofuran are now added to the grey-brown solution at reflux temperature and the mixture is refluxed for a further 90 minutes. The cooled solution is treated with 250 ml of 5-N hydrochloric acid and extracted three times with ether. The combined ether phases are washed three times with water, dried over sodium sulphate and concentrated, there being obtained 133.6 g (96% yield) of 2,5-dimethyl-4-cyano-tetrahydrofuran-3-one of boiling point 109°-111° C./18 Torr. Gas-chromatographical identification (GC) on a 3 m column, 2% Carbowax on Chromosorb: retention times of 2.9 and 3.2 minutes are measured at 200° C. (diastereomeric mixture); $N_{20}^D = 1.450$.

(b) 7 g of the foregoing cyclic nitrile and 21 g of sodium bicarbonate are dissolved in 400 ml of water in a flask, treated at 10° C. with a solution of 25 g of Caroat (Degussa) in 80 ml of water and, after 30 minutes, extracted four times with 150 ml of ethyl acetate each time. The combined organic phases are dried over sodium sulphate and concentrated, there being obtained 4.3 g (55% yield) of a diastereomeric mixture of 2,5-dimethyl-4-hydroxy-4-cyano-tetrahydrofuran-3-one of boiling point ca 95° C./0.04 Torr; $n_{20}^D = 1.468$; IR: 3400 nm (strong), 3010 nm, 2970 and 2910 nm (doublet), 2280 nm (weak), 1780 nm (medium), 1385 nm (strong), 1110 nm (strong).

(c$_1$) 5 g of the foregoing cyanohydrin and 7.5 g of ion exchanger Dowex 2 (OH$^\ominus$ form) are refluxed in 30 ml of water for 1 hour and then the mixture is filtered. The filtrate is saturated with sodium chloride and extracted four times with 80 ml of ethyl acetate each time. The combined organic phases, dried over sodium sulphate, are concentrated and give 2 g (50% yield) of an oil which crystallises out upon standing. Identity with 4-hydroxy-2,5-dimethyl-3(2H)-furanone is established by thin-layer chromatography and NMR.

(c$_2$) 1 g of the foregoing cyanohydrin and 0.7 g of triethylamine are refluxed in 10 ml of toluene for 15 minutes. 5 g of Kieselgel (Merck) are now added and the mixture is filtered. The concentrated solution gives 0.34 g of 4-hydroxy-2,5-dimethyl-3(2H)-furanone.

EXAMPLE 2

(a) 72.6 g (0.55 mol) of butyl glycolate are added dropwise to 12 g (0.5 mol) of sodium hydride in 500 ml of tetrahydrofuran. The resulting green-brown mixture is treated at reflux temperature with 36.9 g of crotonic acid nitrile in 50 ml of tetrahydrofuran and the mixture is held at reflux temperature for 90 minutes. The cooled mixture is adjusted to pH 9 with sodium bicarbonate solution and washed three times with ether. The aqueous phase is acidified to pH 1 with hydrochloric acid and extracted four times with ether. The dried and concentrated ether phases give 29.1 g of 4-cyano-5-methyl-tetrahydrofuran-3-one of boiling point 112°-116° C./13 Torr; GC (Carbowax, 180° C.) one peak; IR (film): 2250 (multiplet CN); 1783 (singlet, C=O).

(b) 3.1 g of the foregoing cyclic nitrile, 10.5 g of sodium bicarbonate and 2 g of sodium hydroxide are dissolved in 30 ml of water in a flask and treated at 15°-20° C. with a solution of 11 g of Caroat (Degussa) in 35 ml of water. After 30 minutes, the mixture is extracted five times with 35 ml of ethyl acetate each time and the combined ethyl acetate phases are dried and concentrated. There are obtained 2.2 g (63% of theory) of 4-cyano-4-hydroxy-5-methyl-tetrahydrofuran-3-one in the form of a light-brown oil; GC: one peak; NMR (CDCl$_3$) shows complex multiplets between 3.3-4.7 ppm and 1-1.8 ppm as well as one OH signal at 5.7 ppm.

(c) 1.07 g of the resulting cyanohydrin and 2.0 g of sodium gluconate are refluxed in 15 ml of water for 15 minutes. The mixture is extracted five times with ethyl acetate, the ethyl acetate phases are dried and concentrated, there being obtained 0.42 g of 4-hydroxy-5-methyl-3(2H)-furanone. The recrystallised material (melting point 111°-120° C.) shows the following NMR (CDCl$_3$): 7.3 ppm (singlet 1H, OH); 4.5-65 ppm (multiplet 3H, CH$_3$).

EXAMPLE 3

(a) 8.7 g (0.2 mol) of sodium hydride are suspended in 100 ml of tetrahydrofuran and the suspension is stirred at room temperature for 90 minutes with 23.6 g (0.2 mol) of ethyl lactate. 9.5 g (0.18 mol) of acrylonitrile are then added dropwise at 60° C. and the mixture is refluxed for 90 minutes. The mixture is poured into 200 ml of water and washed twice with 100 ml of ether each time. The aqueous phase is adjusted to pH 1 with 2-N hydrochloric acid and extracted three times with 150 ml of ether each time. The dried and concentrated ether phases give 20.1 g (89%) of 4-cyano-2-methyltetrahydrofuran-3-one of boiling point 116°-118° C./14 mmHg; IR: 2250 (CN), 1780 (C=O); NMR (CDCl$_3$): 1.37 ppm doublet (CH$_3$); 3.4-4.9 ppm multiplet.

(b) The foregoing product is treated in a manner analogous to that described in Example 2(b). There is obtained in 71% yield 4-cyano-4-hydroxy-2-methyltetrahydrofuran-3-one in the form of the diastereomeric mixture; IR: 3350 (OH); 2290 weak (CN), 1785 and 1730 (C=N); NMR (CDCl$_3$): 1.4-1.7 ppm multiplet (CH$_3$); 3.7-4.8 ppm multiplet (3×O—C—H), 7.1 singlet (OH).

(c) 3 g of the resulting cyanohydrin are dissolved together with 2.2 g of sodium acetate in 40 ml of water and the solution is heated to 70° C. for 15 minutes. The mixture is then extracted five times with 50 ml of methylene chloride each time. The dried and concentrated methylene chloride phases give 150 mg (6%) of crystalline 4-hydroxy-5-methyl-3(2H)-furanone, which is identical with the product obtained according to Example 2(c).

EXAMPLE 4

(a) 2.3 g (0.1 mol) of sodium are dissolved in 50 ml of isopropanol and, while cooling, the solution is treated with 14.5 g (0.11 mol) of ethyl 2-hydroxybutyrate. 7.4 g (0.11 mol) of crotonic acid nitrile are added dropwise at reflux temperature and subsequently the mixture is refluxed for a further 90 minutes. The mixture is poured into 100 ml of water and washed twice at pH 11 with 100 ml of methylene chloride each time. The aqueous phase is adjusted to pH 1 with concentrated hydrochloric acid and extracted five times with 100 ml of methylene chloride each time. The combined organic phases are dried over sodium sulphate and concentrated to give 10.2 g (66%) of 2-ethyl-4-cyano-5-methyl-tetrahydrofuran-3-one (diastereomeric mixture) of boiling point 254° C.; IR: 2370 (C≡N); 1775 (C=O); MS: 153; 138; 125; 68 (100%).

(b) 6 g of the foregoing nitrile are dissolved together with 3.8 g of borax and 3.2 g of sodium hydroxide in 40 ml of water and the solution is treated portionwise with 17 g of Caroat. After 30 minutes, the mixture is acidified with dilute sulphuric acid (1:1) and extracted four times with 50 ml of ethyl acetate each time. After drying and concentration, there are obtained 5.5 g (83%) of 2-ehtyl-4-cyano-4-hydroxy-5-methyl-tetrahydrofuran-3-one; IR: 3550 (OH), 2240 weak (CN), 1780 and 1720 (C=O); NMR (CDCl$_3$): 0.8–2.2 ppm multiplet, 3.5–4.9 ppm multiplet, 6.2 singlet (OH).

(c) 5 g of the product obtained according to the preceding paragraph are dissolved in 40 ml of water and the solution is adjusted to pH 1 with 2-N sulphuric acid. After refluxing for 4 hours, the mixture is cooled down and extracted five times with 50 ml of methylene chloride each time. The methylene chloride phases are dried over sodium sulphate and concentrated to give 2.6 g (63%) of a mixture of 2-ethyl-4-hydroxy-5-methyl-3(2H)-furanone and 5-ethyl-4-hydroxy-2-methyl-3(2H)-furanone; MS: 142 (100%), 127, 114, 99, 85, 71, 57, 4; IR: 3250 (OH), 1690 (C=O), 1615 strong (C=C).

EXAMPLE 5

(a) When there are used in Example 1(a) in place of the crotonic acid nitrile 89.1 g (1.1 mol) of 2-pentenoic acid nitrile [prepared according to D. Mac Peek et al, J. Am. Chem. Soc. 81, 680 (1959)], there is obtained in 54% yield 5-ethyl-4-cyano-2-methyl-tetrahydrofuran-3-one; n$_D^{20}$=1.4552; IR: 2250 (CN), 1778 (C=O); MS: 153, 125, 96, 82 (100%).

(b) The resulting nitrile is treated with Caroat in a manner analogous to that described in Example 1(b) and gives in 83% yield viscous 5-ethyl-4-cyano-4-hydroxy-2-methyltetrahydrofuran-3-one; n$_D^{20}$=1.4587; IR: 3400 (OH), 2240 (weak, CN), 1785 (C=O); MS: 142 (M—HCN), 114, 97, 82, 70 (100%).

(c) The cyanohydrin is treated in a manner analogous to that described in Example 1(c). There is obtained in 84% yield 5-ethyl-4-hydroxy-2-methyl-3(2H)-furanone. N$_D^{20}$=1.5071. The ester isomerises partially upon standing [see Example 4(c)].

EXAMPLE 6

(a) When, in Example 3(a), the ethyl lactate is replaced by ethyl α-hydroxybutyrate and the acrylonitrile is replaced by 2-pentenoic acid nitrile [prepared according to D. Mac Peek et al, J. Amer. Chem. Soc. 81, 680 (1959)], then there is obtained, in addition to a small amount of dimeric pentenoic acid nitrile (which can be separated from the basic phase), in 50% yield 2,5-diethyl-4-cyanotetrahydrofuran-3-one; n$_D^{20}$=1.4538; IR: 2250 (CN); 1775 (C=O). NMR (CDCl$_3$): 3.5–4.6 m/2 pr (H2, H5); 3.25 d and 3.08 d/1 pr (H4); 1.4–2.1 m/4 pr (2×CH$_2$); 0.8–1.3 m/6 pr (2×CH$_3$); MS: 167 (M+), 139, 82 (100%).

(b) The resulting nitrile is oxidised in a manner analogous to that described in Example 2(b). There is obtained in 79% yield viscous 2,5-diethyl-4-cyano-4-hydroxytetrahydrofuran-3-one; n$_D^{20}$=1.4588; IR: 3300 (OH) 2240 (weak, CN), 1782 (C=O); MS: 156 (M—HCN), 97, 82, 70 (100%).

(c) The resulting cyanohydrin is cleaved in a manner analogous to that described in Example 3(c). There is obtained in 75% yield 2,5-diethyl-4-hydroxy-3(2H)-furanone of boiling point 50°–55° C./0.03 mmHg. After recrystallisation from diisopropyl ether, the melting point is 94°–96° C.; IR: 3250 (OH), 1690 (C=O), 1620 (C=C); NMR (CDCl$_3$): 7.3 ppm s/1 pr (OH), 4.37 tr broad/1 pr (H2), 2.65 quart/2 pr (CH$_2$ at C5), 1.5–2.2 m/2 pr (CH$_2$ at C2), 0.8–1.4 2×tr/6 pr (2×CH$_3$); MS: 156 (M+), 141, 99, 71, 58 (100%).

EXAMPLE 7

(a) If, in Example 3(a), the ethyl lactate is replaced by ethyl α-hydroxybutyrate, then there is obtained in 68% yield 2-ethyl-4-cyanotetrahydrofuran-3-one; n$_D^{20}$=1.4641; IR: 2260 (CN), 1775 (C=O); MS: 139 (M+), 111 (M—CO), 107, 57, 54 (100%).

(b) The nitrile is oxidised in a manner analogous to that described in Example 2(b). There is obtained in 50% yield 2-ethyl-4-cyano-4-hydroxytetrahydrofuran-3-one in the form of a yellow oil; n$_D^{20}$=1.4586; IR: 3400 (OH), 2250 (weak, CN), 1783 (C=O); NMR (CDCl$_3$): 4.70 ppm d/1 pr (H5), 3.9–4.4 m/2 pr (H2 and OH), 3.88 d/1 pr (H5), 1.5–2.2 m/2 pr (CH$_2$ at C2), 1.05 tr/3 pr (CH$_3$).

(c) The resulting cyanohydrin is treated in a manner analogous to that described in Example 2(c). There is obtained in 41% yield 5-ethyl-4-hydroxy-3(2H)-furanone of melting point 47°–48° C. (from diisopropyl ether); IR (chloroform): 3250 (OH), 1710 (C=O), 1620 (C=C); NMR (CDCl$_3$): 6.4 ppm s broad/1 pr (OH), 4.53 s/2 pr (H2), 2.69 quart/2 pr (CH$_2$ at C5), 1.27 tr/3 pr (CH$_3$).

What is claimed is:

1. Compounds of the general formula

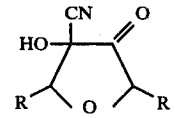

wherein R represents a hydrogen atom or the methyl or ethyl group.

2. A compound in accordance with claim 1, having the formula:
  2,5-dimethyl-4-cyano-4-hydroxy-tetrahydrofuran-3-one.

3. A compound in accordance with claim 1, having the formula:
4-cyano-4-hydroxy-5-methyl-tetrahydrofuran-3-one.

4. A compound in accordance with claim 1, having the formula:
2-ethyl-4-cyano-4-hydroxy-5-methyl-tetrahydrofuran-3-one.

5. A compound in accordance with claim 1, having the formula:
4-cyano-4-hydroxy-2-methyl-tetrahydrofuran-3-one.

6. A compound in accordance with claim 1, having the formula:
5-ethyl-4-cyano-4-hydroxy-2-methyl-tetrahydrofuran-3-one.

7. A compound in accordance with claim 1, having the formula:
2,5-diethyl-4-cyano-4-hydroxy-tetrahydrofuran-3-one.

8. A compound in accordance with claim 1, having the formula:
2-ethyl-4-cyano-4-hydroxy-tetrahydrofuran-3-one.

* * * * *